United States Patent
Lee

(10) Patent No.: US 6,520,924 B2
(45) Date of Patent: Feb. 18, 2003

(54) AUTOMATIC DIAGNOSTIC APPARATUS WITH A STETHOSCOPE

(76) Inventor: Byung Hoon Lee, #7-402, Jinhung Apt., 65 Cheongdam-dong., Kangnam-ku, Seoul 135-100 (KR)

( * ) Notice: Subject to any disclaimer, the term of this patent is extended or adjusted under 35 U.S.C. 154(b) by 69 days.

(21) Appl. No.: 09/865,974

(22) Filed: May 25, 2001

(65) Prior Publication Data

US 2002/0058889 A1 May 16, 2002

(30) Foreign Application Priority Data

Nov. 16, 2000 (KR) ........................................ 2000-68124

(51) Int. Cl.[7] .............................................. A61B 5/08
(52) U.S. Cl. ...................................... 600/586; 600/485
(58) Field of Search ................................ 600/485, 500, 600/504, 509, 522, 523, 528, 532, 538, 586; 181/131, 132; 381/67, 92

(56) References Cited

U.S. PATENT DOCUMENTS 4,720,866 A * 1/1988 Elias et al. .................. 600/522
5,844,997 A * 12/1998 Murphy, Jr. ................ 600/529
6,261,238 B1 * 7/2001 Gavriely .................... 600/532

* cited by examiner

Primary Examiner—Tu Ba Hoang

(57) ABSTRACT

An automatic diagnostic apparatus with a stethoscope is disclosed in which the name of a disease is automatically determined and recorded based on auscultated sounds. Standard data of auscultated sounds for cardiovascular diseases, respiratory diseases and gastrointestinal diseases are inputted into a computer beforehand. Then the waveforms of the auscultated sounds from stethoscoping a patient are converted into digital data and inputted into a computer, and the digital data signals are compared, with searches, with the standard data which have been inputted into the computer in advance. By this process the names of diseases are determined, and the names of diseases thus determined are automatically recorded in a recording device and displayed on monitors so that treatment can initiate swiftly with enhanced credibility of the objective diagnostic process through consensus between the physician and the patient.

4 Claims, 2 Drawing Sheets

AUTOMATIC DIAGNOSTIC APPARATUS WITH A STETHOSCOPE

FIELD OF THE INVENTION

The present invention relates to an automatic diagnostic apparatus with a stethoscope, which automatically reads and records the name of the disease of a patient by auscultated sounds and enables the recorded data to be monitored by the physician, patient, and others concerned.

BACKGROUND OF THE INVENTION

Conventionally, cardiovascular diseases, respiratory diseases and gastrointestinal diseases were distinguished according to the sounds asculated from the body of a patient and the degree of the seriousness of a disease was assessed by such sounds.

If a precise diagnosis was to be made by the auscultated sounds, an extensive empirical knowledge of various and diverse forms of auscultated sounds was necessary. Moreover, a patient had to be examined closely over a long period of time. However, in practice, a physician had to see many patients each day, and the time the physician had to spare for each patient was short, making it difficult, in many cases, to diagnose the patient swiftly and accurately.

Furthermore, a considerable number of patients were incredulous of the results of the physician's diagnosis offhand, and therefore, patients wandered through several hospitals until there were satisfied by the same diagnosis given by them. Thus, many patients spent unnecessarily long times before they made a decision to be treated by a physician, losing, more often than not, an opportunity for an early and effective treatment.

The diagnosis should be speedy and accurate, but conventional methods of examining a patient took a physician a prolonged period of time, relying on his or her rather subjective knowledge, resulting often in young and inexperienced physicians giving an erroneous diagnosis.

In the case of an electrocardiogram examination, the name of the disease is made available automatically as soon as the electrocardiogram examination is completed by the machine reading the information contained in the electrocardiogram, helping the physician to make a diagnosis precisely and conveniently.

However, in the examination of a patient by means of a stethoscope, as there is no apparatus for reading the name of a disease by the sounds of auscultation, the physician diagnoses a patient based on his personal knowledge and experience.

SUMMARY OF THE INVENTION

The present invention is intended to overcome the above-described disadvantages of conventional techniques for auscultation.

It is an object of the present invention to provide a diagnostic apparatus by which the name of the disease is automatically read and recorded based on the auscultated sounds, while making it possible to monitor the examination results.

It is another object of the present invention to provide a diagnostic apparatus, which enables both the physician and the patient to monitor the result of the examination in order to take quick action to treat the disease through mutual awareness of the patient's disease between the physician and the patient.

In achieving the above objects, the diagnostic apparatus according to the present invention includes:

a stethoscope with a microphone for inputting the auscultated sounds from a patient;

a filter for filtering the auscultated sounds; an amplifier for amplifying the filtered auscultated sounds;

a digital converter for digitizing the waveform data of the amplified auscultated sounds;

a computer for inputting the converted waveform data of auscultated sounds and comparing them with the standard data information of auscultated sounds, inputted beforehand, of respiratory diseases, cardiovascular diseases and gastrointestinal diseases; and a computer output recording device and a device for reading, recording, and diagnosing the auscultated sounds of the present invention displayed on a monitor.

The physician, following the ordinary process of examining a patient, auscultates a patient on various portions of the patient's body in a set sequence, auscultating the patient under various circumstances, changing the position of the patient appropriately, to obtain the auscultatory sound data.

The auscultated sound data obtained by the stethoscope microphone is filtered through a filter, which filters the noise that comes from outside the patient's body before the auscultated sounds are amplified. The analogue waveform of the amplified auscultated sounds are converted to digital data though a digital converter, and this digital data is inputted into a computer.

The auscultated digital data thus inputted into the computer is compared through searches with the standard data information of auscultated sounds of various diseases, which have already been inputted in the computer beforehand, and then a relevant disease name is pinpointed and outputted to the monitor of the computer.

The outputted name of disease is automatically recorded in the recording device, and the recorded data can be outputted repeatedly. The recorded name of the disease can be viewed by the physician; the nurses, the patient and the family of the patient, and by others. Thus, a required treatment can start swiftly with consensus among all concerned.

According to the present invention, the name of the disease is decided not by the physician's own personal judgment alone, but with the help of the result of the search and comparison of the various data of the newly auscultated sounds by the computer with the standard data information inputted beforehand, thereby preventing the possible misjudgment of the physician resulting from his inexperience and lack of knowledge. The credibility of the result of the examination and the diagnosis is thereby enhanced. As a precise name of the disease is available through an objective process, the treatment of the disease can begin with greater certainty and swiftness, thus helping the physician to undertake the treatment with greater confidence more speedily and accurately, thereby improving and expediting the chances of the patient's recovery from the disease.

BRIEF DESCRIPTION OF THE DRAWINGS

The above objects and other advantages of the present invention will become more apparent by describing in detail the preferred embodiments of the present invention with reference to the attached drawings in which.

DETAILED DESCRIPTION OF THE PREFERRED EMBODIMENTS

Figure 1:
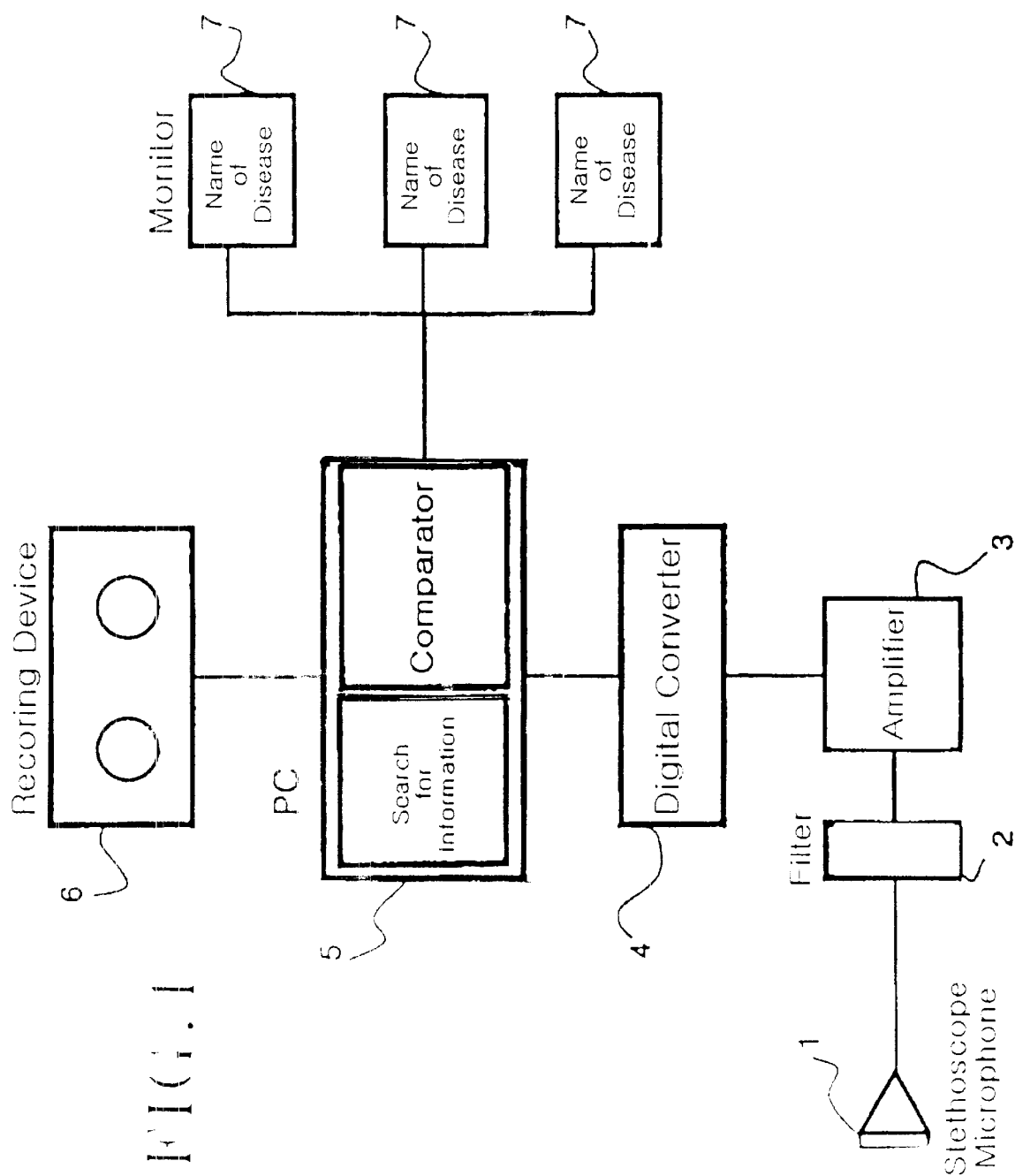
FIG. 1 is a block diagram showing the constitution of the diagnostic apparatus according to the present invention.

FIG. 1 is a block diagram showing the constitution of the diagnostic apparatus according to the present invention.

As shown in this drawing, the diagnostic apparatus according to the present invention comprises;

- a stethoscope microphone 1 for inputting into the computer the auscultated sounds from a patient;
- a filter 2 for filtering the noise coming from outside the patient's body from the auscultated sounds inputted from the stethoscope microphone;
- an amplifier 3 for amplifying the frequency of the auscultated sounds filtered by the filter 2;
- a digital converter 4 for converting the analogue waveform of the amplified auscultated sounds to a digitalized form;
- a computer 5 for inputting the data of the auscultated sounds digitalized by the digital converter 4 for search and comparison with the standard information data inputted beforehand; and
- a recording device 5 for automatically recording the output from the computer, and a plurality of monitors 7 for displaying the name of the disease.

Inputted into the computer are standard data of auscultated sounds of respiratory diseases, cardiovascular diseases and gastrointestinal diseases.

The auscultated sounds from the stethoscope which the physician applied on the body of the patient are inputted into the computer through a microphone 1 attached to a stethoscope, and the auscultated sounds are filtered by a filter to remove the noises from outside the patient's body, and the frequency of the auscultated sounds is amplified. The analogue waveforms of the amplified auscultated sounds are converted into digital signals by the digital converter 4 and then the converted digital data signals are inputted into the computer. The digital data thus inputted into the computer is compared through a search operation with the standard auscultated sound data inputted beforehand for outputting the disease name in relevance, which then is automatically recorded in a recording device and displayed on a plurality of monitors at the same time for viewing by the physician, the patient, and others, such as the physician's assistants, and the patient's family. The recorded data signals are used for diagnosis and treatment of the patent.

EXAMPLE 1

Auscultated Sound of the Cardiovascular System

Auscultation Area of Cardiovascular System

The areas in which the sounds from the valves of the heart are auscultated best are noted below. The difference between these positions and the anatomical positions of the valves of the heart is due to the fact that the sounds are transmitted through the circulating blood and through the skin of the body where the sound is best transmitted.

The auscultation positions are as follows:

Aortic valve area: right sternal border at $2^{nd}$ intercostals space.

Pulmonary valve area: left sternal border at $2^{nd}$ intercostals space.

Tricuspid valve area: left lower sternal border;

Mitral valve area: cardiac apex; and

Erb's area: left sternal border at third intercostals space. (This is the position where the cardiac murmur is best heard in the case of aortic insufficiency).

Position for Auscultation

The auscultation should be carried out with a patient in a comfortable posture, and clothes ought to be taken off to avoid external noises, while the patient breathes calmly and naturally.

Most of the cardiac sounds and cardiac murmurs are well auscultated in a supine position, while the sounds from the base of the heart are better auscultated in a sitting position.

The cardiac murmurs due to aortic insufficiency are best auscultated when the patient is seated and slightly inclines himself forward, while the third and fourth cardiac sounds and the cardiac murmurs due to mitral stenosis can often be auscultated only when the patient lies with his left chest down.

Heart Sounds

Figure 2:
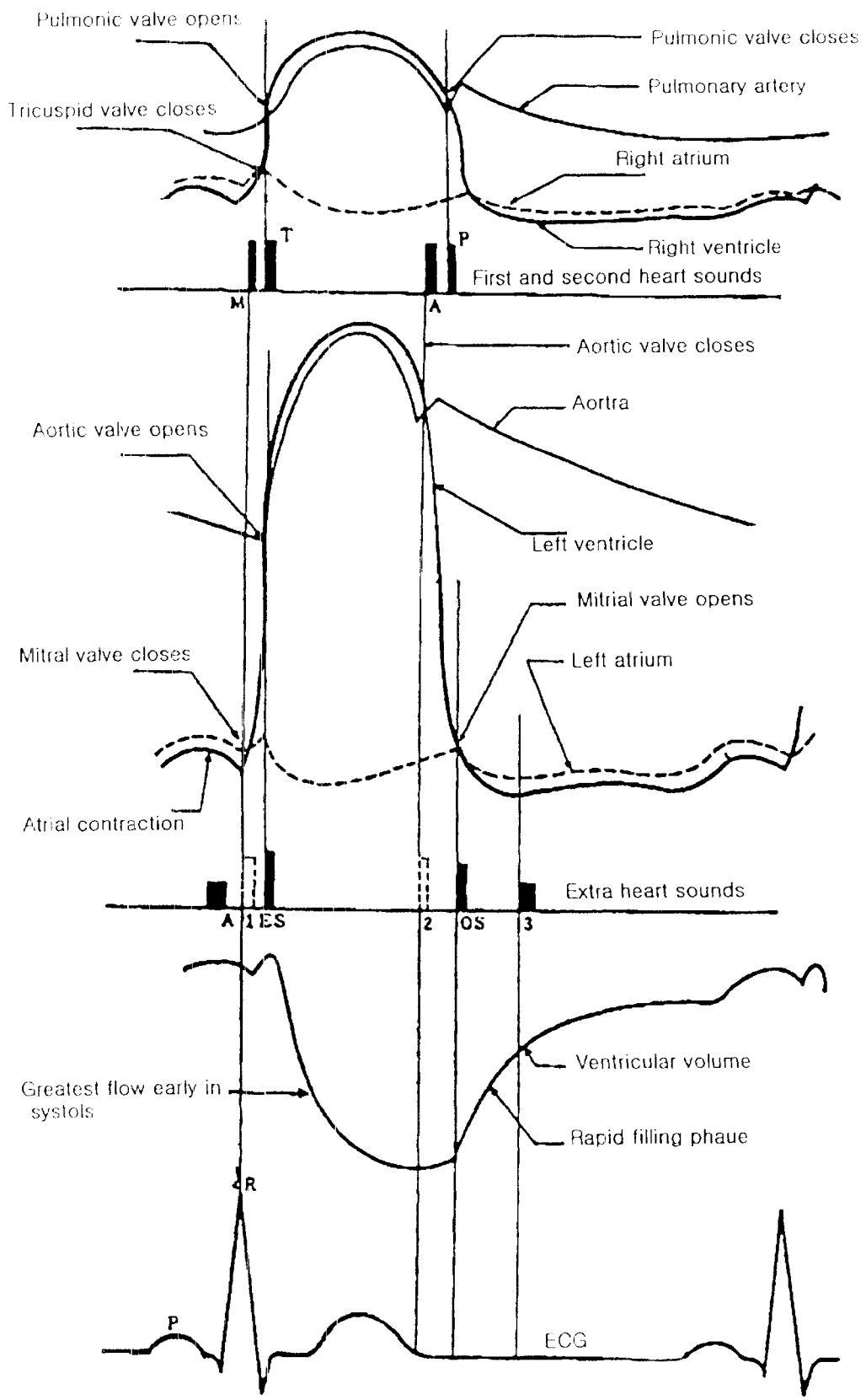
FIG. 2 illustrates the waveforms of the cardiac sounds matched with an electrocardiogram.

In order to understand the time points at which the first, second, third and fourth heart sounds occur in the cardiac cycle, as well as their mechanism of heart sound development, one ought to understand the electric force, the mechanical changes of the blood stream, and the relationship between the heart sounds as shown in FIG. 2.

First Heart Sound

The first heart sound is generated when the mitral valve and the tricuspid valve are closed, and the sound is a little lower and longer than the second heart sound. The closing sound of the mitral valve is generated slightly earlier than the closing sound of the tricuspid valve, but as the interval between them is very short, they are usually heard like a single sound.

Second Heart Sound

The second heart sound is generated when the aortic valve and the pulmonary artery valve are closed. Normally, the closing sound of the aortic valve $A_2$ earlier than the closing sounds of the pulmonary artery valve $P_2$.

In inhalation, the interval between $A_2$ and $P_2$ is shortened, and this phenomenon is called "normal splitting." In contrast, when a long interval is maintained regardless of respirations, it is called "fixed splitting of $S_2$."

Third Heart Sound

The third heart sound is generated during the expansion period of diastolic rapid ventricular filling period when blood is pushed in from the atrium into the ventricle to abruptly expand the walls of the ventricle. Therefore, the magnitude of the third heart sound is decided by the preload, the left atrial pressure, and the compliance of the ventricle muscle. The third heart sound is auscultated in most cases as a normal phenomenon in adolescents, but it is regarded as a pathological symptom in adults. The third heart sound is generated at 0.10–0.20 seconds following $A_2$, and as it is a low sound, auscultation should be made with the bell of the stethoscope touching the skin lightly.

Fourth Heart Sound

This is a very low sound, which is generated by the contraction of the atrium and is auscultated immediately before the first heart sound. This is not necessarily a pathological symptom, but it is auscultated in most cases when the left ventricular diastolic blood pressure has risen or when the expansion of the ventricles has decreased, as seen in the case of hypertension and the disorder of the aortic valve.

Ejection Click

This is a high sound, which is generated when the aorta or the pulmonary artery is abruptly expanded.

Mid Systolic Click

This is a sound generated when there is mitral valve prolapse

Cardiac Murmurs

Description of cardiac murmurs:

The cardiac murmurs ought to be described in the following four aspects: (a) systolic murmur or diastolic murmur? (b) intensity of murmur (?) (c) on which area is the auscultation made? (d) where does the murmur propagate to?

The intensity of the cardiac murmur is graduated into I: very faint; II: faint; III: moderately loud, IV: loud (thrill+); V: very loud, VI: extra high loud (auscultation is needless).

Classification of Cardiac Murmurs

Cardiac murmurs occur by the eddy current formed between the two chambers with different pressures.

The pan-systolic murmurs is that which starts simultaneously with the first heart sound to continue to the second heart sound with a constant level of intensity.

The ejection murmur is that which starts following the first heart sound and continues with growing intensity, the peak of the intensity reaching in the middle of the systolic period, the intensity diminishing gradually, and the ejection murmur terminates before the second heart sound.

Early systolic murmur is a rare phenomenon. It is auscultated in a ventricular septum loss symptom in which the closing is done at the late systolic period.

The late systolic murmur is due to a light mitral valve disorder in almost all cases.

Diastolic Murmur

The early diastolic murmur starts immediately after the second heart sound and its intensity diminishes gradually, as seen in the case of the aortic insufficiency.

The mid-diastolic murmur starts at a certain interval with the end of the second heart sound and continues briefly or to the end of the diastolic period.

The presystolic murmur starts at the late diastolic period with its intensity reaching its peak immediately before the first heart sound. The presystolic murmur occurs because the blood flow increases through the constricted mitral vale or tricuspid valve by the contraction of the heart.

Continuous Murmur

This murmur is auscultated continuously over the systolic and diastolic periods, and occurs when a corridor is formed between two portions between which a great different in pressure continues over the entire heart cycle. An instance of this is the patient ductus arteriosus.

The auscultated sounds, which are captured in Example 1 of the present invention, are analyzed by the computer when they are inputted into the computer through aforesaid microphone attached to the stethoscope, and the name of the disease is recorded in a recording device and displayed on the monitor, thus preventing the chances of the physician's misjudgment.

EXAMPLE 2

Auscultation of the Respiratory System

The auscultated sounds of the respiratory system, in contrast with the heart sounds, is such that the flatness is extremely short and of a high pitch, as is seen in the case of a massive pleural fluid of pleurisy and an atelectasis. The dull portion is short, of a high pitch and has no resonance. This is auscultated as a normal symptom at the boundary between the heart and lung, at the boundary between the lungs, at the boundary between the lung and the spleen, and in the mediastinum portion and is observed as a pathological symptom in atelectasis.

Method of Auscultation

The auscultation can give judgment on the air flow, the presence or absence of an obstruction, and the condition between the lungs and the pleura. In carrying out the auscultation, the patient is made to deeply and strongly inhale, and the auscultation is carried out symmetrically between the left and right lungs, beginning at the upper portion of the lungs, by placing the diaphragm of the stethoscope on the relevant portions.

Breath Sound

The kinds of auscultated sounds of the respiratory system are as follows:

In vesicular breathing, inspiration is longer than expiration and is observed in a person in normal conditions.

In bronchial breathing, expiration is longer than expiration, and the breath sound is loud and coarse, which is caused by the increase in the propagation of respiratory sounds due to lung parenchymal consolidation or a pressure of lung parenchyma.

Tracheal breathing is similar to the bronchial breathing, but is auscultated in a person of normal conditions at the $6^{th}$ and $7^{th}$ cervical vertebrae.

In broncho-vesicular breathing, which occurs between vesicular and bronchial area, inspiration and expiration are of the same length. This is auscultated at the chest bones and at the upper interscapular area in a person in normal conditions, and is auscultated as a morbid symptom in a small degree of long parenchymal consolidation or a pressure of lung parenchyma.

Adventitious Sound

Crackle crepitation, which is an adventitious sound, is an explosive sound and has a frequency of 200 Hz to 2000 Hz, and is observed mainly in inspiration.

Crackle crepitation occurs when a pressure difference between collapsed lung cells is momentarily dissipated during inspiration. Crackle crepitation is classified into "fine," "medium" and "coarse," based on its intensity, and is classified into "late inspiratory" and "early inspiratory," based on the respiratory period.

Late inspiratory crackle occurs in the diseases which cause the obstruction of the fine bronchial branches. Late inspiratory crackle does not dissipate, even after a cough. Late inspiratory crackle is in most cases in a "fine crackle" class.

Early inspiratory crackle has a low pitch in sound compared with later inspiratory crackle and is influenced by coughing. Early inspiratory crackle is observed in chronic obliterative lung disease and in a serious heart failure and the sound is coarse.

Wheeze is a sound which contains 250 m/sec or more, and is auscultated mostly during expiration. Wheeze occurs due to a vibration of the respiratory channels, and its sound pitch varies depending on the size and compliance of the respiratory channels and on the velocity of the air that flows. The continuous sounds are all called "wheeze."

Stridor is a special type of wheeze and is more clearly auscultated during inspiration and is observed in a partial extrathoracic upper airway obstruction. Therefore, this is helpful in diagnosing larynx, tracheal and bronchial obstruction.

Voice Sound

Voice sound is auscultated in a person in normal conditions as a confused sound, in which case the words are not clearly distinguishable. However, in a morbid state, a variation occurs in the voice propagation and helps a physician to diagnosis.

Bronchophony is heard from the large bronchi, and the sound is larger than in the normal case and is heard more clearly and closely to the ear than in the normal case, but is not clearly distinguishable.

Bronchophony occurs when the air in lung chambers has decreased due to the partial closing of the bronchi because of lung parenchymal consolidation, atelectasis or an externally caused tumor, causing a high-pitch sound to be propagated well. This has a meaning as pectoral fremitus. If bronchophony is heard, the sound of pectoral fremitus is increased, and a dull percussion symptom occurs, while lung cell sounds and bronchial sounds can be observed during inspiration upon auscultation.

Pectoriloquy is hardly heard in a whispered speech in a normal case, as it is propagated weakly. However, in the presence of a lung parenchymal consolidation, the whispered speech is clearly auscultated.

Pectriloquy is helpful for diagnosing a lung parenchymal consolidation, and particularly for diagnosing an early pneumonia, lung infarction, and atelectasis.

Egophony is a variation of bronchophony and is low in the resonance and high in the pitch, sounds like a nasal sound like the bleating of a goat.

As this sound is auscultated when a lung consolidation has occurred because the lung immediately below the pleural water is pressed, this sound is helpful for distinguishing between a simple consolidation and the lung consolidation accompanying the pressing of pleural water.

Friction Sound

This sound is produced by the frictions between the visceral pleura and the parietal pleura during respiration if the pleural surface has become rough due to pleurisy. If an auscultator is press-contacted on the chest wall, the sound becomes more intense, and the sound is well heard at the anterolateral or lateral based thorax. If the friction sound is intense, it could aggravate vibration.

The auscultated sounds which are captured in Example 2 of the present invention need not be interpreted subjectively by the physician, but the data are inputted into a computer through a microphone of the stethoscope as mentioned above so as to be analyzed by the computer, the name of the disease being displayed on the monitors and recorded in the recording device.

EXAMPLE 3

Auscultation of Gastrointestinal System

The auscultatable sounds of the gastrointestinal system are as follows:

By deciding the presence or absence, as well as its characteristic, of a peristaltic sound, the relationship between the intestinal movements and the symptom can be clarified.

Different from examination on other parts of abdomen, an auscultation is made after a visual examination and before palpation and percussion.

When auscultating the peristalsis sound, special attention should be paid to the frequency and the quality of the bowel sound. In the case of a paralytic ileus, the bowel sound is not heard, while in the case of a mechanical obstruction, the sound grows larger and is heard as a metallic sound at the peak of pain.

Bruit is auscultated in a person who has a high blood pressure by auscultating the deep portion of the abdomen by pressing the stethoscope firmly against the abdominal wall and the upper left and right abdominal areas. If a lower extremity cardiovascular abnormality is suspected, auscultations should be made on the large artery, the iliac artery and the femoral artery area as well.

If there is an infection or an infarction, a friction sound is heard at the liver or at the spleen area.

In the case of pylorostenosis, if the abdominal wall is oscillated, a splash is heard.

The auscultated sounds which are captured in Example 3 of the present invention need not be interpreted subjectively by the physician but the data for the auscultated sounds is inputted into a computer through a microphone of the stethoscope as mentioned above so as to be analyzed by the computer, the name of the disease being displayed on the monitors and recorded in the recording device.

According to the present invention as described above, the auscultated sounds are converted into digital data, and the digital data signals are compared, with searches, with standard auscultation sound data information of various diseases which have been inputted into a computer in advance. By so doing, the names of the diseases are determined and outputted and recorded in the computer for display on the monitors. Therefore, the subjective opinions of the physician resulting from the difference in the ability and experience between individual physicians cannot intervene, enhancing the credibility of the result of the examination that came about by this objective process. As the precise name of the disease is made available, diagnosis can be made quickly and accurately. As the patient and his family have greater trust in the diagnosis given, treatment can initiate more swiftly.

Furthermore, as the result of the diagnosis can be viewed simultaneously by the physician, his assistants, the patient and the family of the patient, it further enhances the efficiency of treatment.

What is claimed is:

1. An automatic diagnostic apparatus with a stethoscope which automatically records the name of a disease of a patient and displays the name of the disease on monitors by auscultation comprising:

- a stethoscope with a microphone 1 for auscultating a patient and inputting auscultated sounds;
- a filter 2 for filtering the noise coming from outside the body of a patient from the auscultated sounds inputted through said stethoscope microphone 1;
- an amplifier 3 for amplifying the frequency of the auscultated sounds filtered by said filter 2;
- a digital converter 4 for converting the analogue waveform data of the amplified auscultated sounds into digital data;
- a computer 5 for inputting the digital data of the auscultated sounds converted by the digital converter 4 for comparison, with search operations, with the standard data of the auscultated sounds of various diseases inputted beforehand;
- a recording device 6 which automatically records the computer output; and
- a plurality of monitors 7 for displaying the names of diseases.

2. An automatic auscultation diagnostic apparatus, comprising:

- a stethoscope with a microphone for inputting auscultated sounds from a patient;
- a filter for filtering the auscultated sounds;
- an amplifier for amplifying the filtered auscultated sounds;
- a digital converter for digitizing waveform data of the amplified auscultated sounds;

a computer including a database of standard data of auscultated sounds corresponding to various diseases, said computer including means for comparing the digitized waveform data received from said digital converter with the standard data of auscultated sounds corresponding to various diseases and identifying matches therebetween; and a computer output recording device and a device for reading, recording, and diagnosing the auscultated sounds.

3. The apparatus of claim 2 which further includes:

at least one monitor for displaying the names of the diseases corresponding to the matches identified by the computer.

4. The apparatus of claim 2 wherein the database of standard data of auscultated sounds include cardiovascular sounds, respiratory sounds and gastrointestinal sounds.

* * * * *